United States Patent [19]

Griengl et al.

[11] 4,304,785

[45] Dec. 8, 1981

[54] DILIGNOLS AND DILIGNOL-TYPE COMPOUNDS

[76] Inventors: Herfried Griengl, Argenot-Strasse 23, A-8047 Graz; Gabriele Foidl, Dr. Robert-Graf-Strasse 10, A-8010 Graz, both of Austria

[21] Appl. No.: 170,568

[22] Filed: Jul. 21, 1980

Related U.S. Application Data

[63] Continuation-in-part of Ser. No. 20,940, Mar. 15, 1979, Pat. No. 4,256,764.

[30] Foreign Application Priority Data

Mar. 22, 1978 [DE] Fed. Rep. of Germany ....... 2812664

[51] Int. Cl.³ .................... A61K 31/34; C07D 307/81
[52] U.S. Cl. ............................... 424/285; 260/346.73
[58] Field of Search .................. 260/346.73; 424/285

[56] References Cited

PUBLICATIONS

Freudenberg, Brennstaff–Chemie, 44, 328, (1963).

*Primary Examiner*—Henry R. Jiles
*Assistant Examiner*—Bernard Dentz
*Attorney, Agent, or Firm*—Francis A. Keegan

[57] ABSTRACT

Compounds of formula

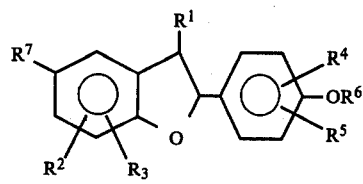

wherein at least one of $R^5$ or $R^6$ bears a substituted amino group, are useful as liver protecting agents.

5 Claims, No Drawings

DILIGNOLS AND DILIGNOL-TYPE COMPOUNDS

This application is a continuation-in-part of our co-pending application Ser. No. 20,940 filed Mar. 15, 1979, now U.S. Pat. No. 4,256,764.

The invention relates to dilignols and chemically affiliated substances, hereinafter called dilignol-type compounds, as active substances of therapeutica for affections of the liver.

The invention further refers to certain new compounds which are suitable for the treatment of liver affections and to methods used in the manufacture of said new compounds.

According to K. Freudenberg (Brennstoff-Chemie 44, 328 [1963]; Adv. Chem. Ser. 59 1 [1966]) oligomeric intermediates of lignin formation are called lignols, which arise during the in vivo or in vitro dehydration of p-cumara, coniferyl or sinapine alcohols and which form special compounds from the class of styrene derivatives with the general formula:

$$Ar-CH=CH-R^1 \qquad (1)$$

($R^1=CH_2OH$; Ar=4-hydroxyphenyl: p-cumara alcohol, Ar=4-hydroxy-3-methoxyphenyl: coniferyl alcohol, Ar=4-hydroxy-3,5-dimethoxyphenyl: sinapine alcohol).

Specifically, the present invention is concerned with dilignol and dilignol type compounds of the general formula

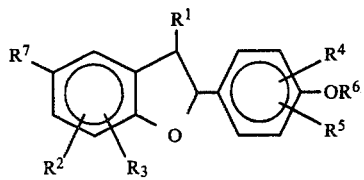

and their salts with pharmaceutically acceptable acids, wherein:

$R^1$ is lower alkyl, $R^2$, $R^3$ and $R^4$ are independently hydrogen, hydroxy or methoxy, $R^5$ and $R^6$ are hydrogen or a lower unbranched or branched alkyl group bearing an amino group substituted by two lower alkyl groups or by lower hydroxyalkyl or carboxyalkyl groups or combinations thereof, with the proviso that not both $R^5$ and $R^6$ are hydrogen and that if one of $R^5$ or $R^6$ is hydrogen, the other is said amino bearing lower alkyl group, and $R^7$ is $-CH=CH-R^1$.

Specific compounds are the following, but other compounds falling within the above general formula are not excluded:

N-[5-(trans-2,3-dihydro-7-methoxy-3-methyl-5-(E)-propenylbenzofuran-2-yl)-2-hydroxy-3-methoxy-phenylmethyl]-N(2-hydroxyethyl)-N-methylammonium-L-aspartate, and the Salt of N-[5-(trans-2,3-dihydro-7-methoxy-3-methyl-5-(E)-propenylbenzofuran-2-yl)-2-hydroxy-3-methoxy-phenylmethyl]-N-(2-hydroxyethyl)-N-methylamine with α-liponic acid, [4-(trans-2,3-dihydro-7-methoxy-3-methyl-5-(E)-propenylbenzofurane-2-yl)-2-methoxyphenoxy]ethyl-N,N-dimethylamine, and its hydrochloride.

N-[5-(trans-2,3-dihydro-7-methoxy-3-methyl-5-(E)-propenylbenzofuran-2-yl)-2-hydroxy-3methoxyphenyl-methyl]-N-methylglycine, N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylamine. and N-[5-(trans-2,3-dihydro-7-methoxy-3-methyl-5-(E)-propenylbenzofuran-2-yl)-2-yl)-2-hydroxy-3-methoxyphenylmethyl]-N-(2-hydroxyethyl)-N-methylammoniumchloride.

The compounds of the present invention may be prepared by any conventional method known per se, but also according to the examples given hereafter, or according to our co-pending application Ser. No. 80,552 filed Oct. 1, 1979, now U.S. Pat. No. 4,256,764.

The compounds have a basic nitrogen atom, and thus can be used in the form of salts with inorganic acids such as hydrochloric, hydrobromic, sulphuric or phosphoric acid or with physiologically compatible organic acids such as formic, acetic, propiolic, succinic, glycolic, lactic, malic, tartaric, citric, dimethyl sulphonic, hydroxydimethyl sulphonic, ethylene sulphonic, ascorbic, lipoic, asparaginic, α-ketoglutaric, glutamic, saccharic, gluconic, mucic or thiazolidinecarbonic acid.

The valuable pharmacological properties of the dilignols and dilignol-type compounds, whose application as active substances of liver therapeutica is the subject matter of the present invention, can be demonstrated in pharmacological experiments.

Standard testing methods for pharmacological effects in experimental affections of the liver are the hexobartibal sleep test, the galactosamine test, and the α-amandine test. They are, for example, described in the study by G. Vogel et al, which appeared in Arzneimittelforschung, volume 25 (1975), pp. 82–89 and 179–188.

In the hexobarbital sleep test, the action of the dilignol-type compound trans-2,3-dihydro-2-(4-hydroxy-3-methoxyphenyl)-7-methoxy-3-methyl-5-(E) propenylbenzofuran ("dehydrodiisoeugenol") is compared with that of the known liver therapeuticum silymarine. For this purpose, rats in groups of 15 animals received intraperitoneally 100 mg/kg of the compound to be tested in carboxymethyl cellulose and 90 minutes later 0.3 ml/kg carbontetrachloride in olive oil by means of a stomach tube. Forty-eight hours later the rats were anesthesized by traperitoneal administration of 70 mg/kg hexobarbital and the sleep period was determined.

|  | min |
|---|---|
| carbontetrachloride without test compound | 128 |
| control (only hexobarbital) | 83 |
| trans-2,3-dihydro-2-(4-hydroxy-3-methoxy-phenyl-7-methoxy-3-methyl-5-(E)-propenyl-benzofuran ("dehydrodiisoeugenol") | 97 |
| silymarine | 115 |

The effect of trans-2,3-dihydro-2-(4-hydroxy-3-methoxyphenyl-7-methoxy-3-methyl-5-(E)-propenyl-benzofuran ("dehydrodiisoeugenol") is highly significant ($p<0.01$), that of the comparator compound silymarine is statistically insignificant.

In another series of experiments, rats received 50 mg/kg 3,6-bis(4-hydroxy-3-methoxyphenyl)tetrahydro-1H,3H-furo[3,4-c]-furan-1,4-dione ("dehydrodiferula acid") and 0.75/ml/kg carbontetrachloride. Implementation of the sleep test after 48 hours as described above yielded for the carbontetrachloride group an average sleep time of 52 minutes, for the group pretreated with dehydrodiferual acid a sleep time of 27.5 minutes, while the control group receiving only hexobarbital showed an average sleep time of 27.4 minutes. Thus, on the basis of these results dehydrodiferula acid causes complete protection against the liver-affecting action of carbontetrachloride.

In the galactosamine test, rats in groups of 15 animals received 100 mg/kg of the new compound N-[5-(trans-2,3-dihydro7-methoxy-3-methyl-5-(E)-propenylbenzofuran-2-yl)-2-hydroxy-3-methoxyphenylmethyl]-N-(2-hydroxyethyl)-N-methylammoniumchloride and, for purposes of comparison, silymarine was administered orally in tragacanth suspension, an hour later 350 mg/kg galactosamine were administered intraperitoneally and 24 hours later blood samples were taken to determine the serum enzyme GOT and GPT.

|  | GOT | GPT |
|---|---|---|
| galactosamine-hydrochloride without test compound | 572 | 578 |
| Control | 113 | 53 |
| N-[5-(trans-2,3-dihydro-7-methoxy-3-methyl-5-(E)-propenylbenzofuran-2-yl))-2-hydroxy-3-methoxyphenylmethyl]-N-(2-hydroxyethyl)-N-methylammoniumchloride | 422 | 185 |
| Silymarine | 794 | 225 |

Particularly in the GPT enzyme the effect of the tested new compound was highly significant ($p < 0.01$) and clearly better than that of silymarine.

In the α-amanitine test, rats in groups of 20 animals received 50 mg/kg N-[5-(trans-2,3-dihydro-7-methoxy-3-methyl-5-(E)-propenylbenzofuran-2-yl)-2-hydroxy-3-methoxyphenylmethyl]-N-(2(2-hydroxyethyl)-N-methylammoniumchloride and for purposes of comparison silymarine was administered intravenously and an hour later 0.7 mg/kg α-amanitine intraperitoneally. The mortality rate was observed for 7 days. Silymarine caused no reduction in the mortality rate as compared with the control group, whereas with N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylammoniumchloride the mortality rate was only 20 percent.

The toxicological experiments showed good compatibility of dilignols and the dilignol-type compounds described above.

As an example, after oral administration in rats LD lies for trans-2,3-dihydro-2(4-hydroxy-3-methoxyphenyl)-7-methody-3-methyl-5-(E)-propenylbenzofuran ("dehydrodiisoeugenol") over 16 g/kg, that for N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methyl-ammoniumchloride between 4–16 g/kg.

Dilignols and dilignol-type compounds are thus valuable highly active substances for liver therapeutica.

The pharmaceutical preparations containing the dilignols or dilignol-type compounds as active substances are valuable liver therapeutica and prophylactica. The dosage of the active substance depends on the circumstances of each individual case, particularly on the type of lesion and, needless to say, on the type of application, but the daily dose is usually between 10 and 1000 mg, especially between 20 and 500 mg and preferably between 25 and 250 mg active substance. The pharmaceutical preparations contain the dilignols or dilignoltype compounds in free form or in the form of their salts, particularly the therapeutically usable salts, usually mixed with a pharmaceutical inorganic or organic carrier material suitable for enteral or parenteral, particularly oral, rectal or intravenous application, for which materials not reacting with the active substances such as water, gelatin, lactose, starch, stearyl alcohol, magnesium stearate, talcum, vegetable oils, benzyl alcohols, rubber, propylene glycols, petroleum jelly and other known therapeutica carriers are employed. The pharmaceutical preparations can be obtained in the form of tablets, pills, capsules, e.g., gelatin capsules, suppositories, or in liquid form such as solvents (e.g. elixir or syrup), suspensions or emulsions. If necessary, they are sterilized and/or contain adjuvants such as preservatives, stabilizers, wetting or emulsifying agents, solubilizers or salts for altering the osmotic pressure or buffers. The may also contain other therapeutically valuable substances. The pharmaceutical preparations are obtained in accordance with conventional methods.

The examples below serve to illustrate the synthesis of new dilignol-type compounds and the manufacture of the pharmaceutical preparations.

EXAMPLE 1

80 g phosphoroxychloride, 14.5 g N,N-dimethylaniline and 30 g trans-2,3-dihydro-2-(4-hydroxy-3-methoxyphenyl-7-methoxy-3-methyl-5-(E)-propenylbenzofuran ("dehydrodiisoeugenol") are kept in 400 ml absolute toluene at room temperature for 12 hours and at 70° C. for 3 hours, then, after cooling separated from the precipitated hydrochloride of the N,N-dimethylaniline, all volatile materials being carefully removed in vacuo at 60° C. The residual viscous oil is treated with 400 ml distilled water and gradually solid sodium carbonate is added at 60° C. with continuous agitation until no more carbon dioxide formation is observed. It is then chilled to room temperature and the pH of the solution is adjusted to 8.5 by the addition of 2 N soda lye. After treatment with 2 liters 96 percent ethanol with vigorous stirring, a white flaky sediment is formed which is immediately separated from the mother liquor and dried in vacuo over $P_4O_{10}$. After repeating this reprecipitation, 33 g disodium-4-[trans-2,3-dihydro-7-methoxy-3-methyl-5-(E)-propenylbenzofuran-2-yl]-2-methoxyphenylphosphate are produced; fine hygroscopic crystals, melting point 185° C.-187° C. (decomposition). $C_{20}H_{21}O_7PNa_2$ (450.16): theoretical: C 53.34, H 4.70, P 6.87, Na 10.21. found: C 52.91, H 4.92, P 6.43, Na 10.02.

Preparation of the starting material:

150 g ferric chloride in 400 ml water are added to a solution of 100 g (E)-isoeugenol in 1.3 liter 75 percent ethanol and allowed to stand for 24 hours at 0° C. The resulting sediment is filtered off and recrystallized from ethanol, resulting in 53 g trans-2,3-dihydro-2-(4-hydroxy-3-methoxyphenyl-7-methoxy3-methyl-5-(E)-propenylbenzofuran ("dehydrodiisoeugenol") as colorless crystals; melting point 132°–133° C.

EXAMPLE 2

5 g (1α, 2β, 3α)-1-ethyl-3-(4-hydroxy-3-methoxyphenyl)-6-methoxy-2methyl-5-indanol ("diisoeugenol") are trickled, with agitation, into a solution of 13.4 g phosphoroxychloride in 20 m absolute pyridine and stirred for 12 hours at room temperature and for 3 hours at 70° C., then separated, after cooling, from the precipitated pyridinechloride, all volatile substances being carefully removed in vacuo and, finally dried for several hours over KOH. The residual oil is treated with 150 ml distilled water and solid sodiumcarbonate is gradually added at 60° C. with continuous stirring until no more carbondioxide formation is observed. Cooling to room temperature and adjustment of the pH value of the solution to 8.5 by the addition of 2 N soda lye. After filtration of any insoluble materials and treatment with 600 ml 95 percent ethanol, a yellow oil is precipitated from which the supernatant is decanted. The oil is redissolved in distilled water and reprecipitated with ethanol. After the second repetition, a flaky sediment is obtained, which is washed with 95 percent ethanol and, after drying, yields 6.6 g of the tetrasodium salt of the diphosphate of the (1α, 2β, 3α)-1-ethyl-3-(4-hydroxy-3-methoxyphenyl)-6-methoxy-2-methyl-5-indanol; melting point 177°–179° C. (decomposition).

$C_{20}H_{22}O_{10}P_2Na_4$ (576.12): theoretical: C 41.59, H 4.03, P 10.73, Na 15.93. found: C 41.16, H 4.23, P 10.82, Na 15.42.

Preparation of the starting material 110 g isoeugenol are dissolved with stirring in 500 ml methanolic 5 N hydrochloric acid and with reflux for 5 hours. After cooling, the methanolic hydrochloric acid is evaporated in vacuo in a rotation evaporator, then treated with 100 ml methanol and 350 ml distilled water, the resulting sediment is separated. After recrystallization from 95 percent ethanol and subsequently from benzene/petroleum ether (boiling point 60°–80° C.) 55 g (1α, 2β, 3α)-1-ethyl-3-(4-hydroxy-3-methylphenyl)-6-methoxy-2-methyl-5-indanol, melting point 180° C. are obtained.

EXAMPLE 3

5 g trans-2,3-dihydro-2-4(4-hydroxy-3-methoxyphenyl)-7-methoxy-3-methyl-5-(E)-propenylbenzofuran ("dehydrodiisoeugenol") and 1.36 g N-methylglycine are kept in 50 ml ethanol after treatment with 1.22 ml 35 percent formaline solution for 16 hours with reflux action, the same amount of N-methylglycine and formaline solution again being added after 12 hours. After cooling, the resulting sediment is separated and, after recrystallization from methanol water 4.1 g N-[5-trans-2,3-dihydro-7-methoxy-3-methyl-5-(E)-propenylbenzofuran-2-yl)-2-hydroxy-3-methoxyphenylmethyl]-N-methylglycine are obtained; fine white crystals, melting point 140.5–141.5 (decomposition). $C_{24}H_{29}O_6N$ (427.29): C 67.40, H 6.86, N 3.28 (theoretical). C 67.13, H 6.73, N 3.21 (found).

EXAMPLE 4

5 g trans 2,3-dihydro-2-(4-hydroxy-3-methoxyphenyl-7-methoxy-3-methyl-5-(E)-propenylbenzofuran ("dehydrodiisoeugenol"), 0.9 g paraformaldehyde and 2.3 g 2-methylamino ethanol are kept in 60 ml absolute ethanol for 48 hours at 65° C., the solvent is then removed in vacuo and after crystallization of the residue from methylenechloride/petroleum ether (boiling point 60°–80°) 4 g N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylamine are obtained; fine colorless crystals, melting pt. 101°–103° C.

$C_{24}H_{31}O_5N$ (413.31): C 69.68, H 7.58, N 3.39 (theoretical). C 69.59, H 7.51, N 3.17 (found).

EXAMPLE 5

As in Example 4, one obtains from 5 g (1α, 2β, 3α)-1-ethyl-3-(4-hydroxy-3-methoxyphenyl)-6-methoxy-2-methyl-5-indanol ("diisoeugenol") 0.9 g paraformaldehyde and 2.3 g 2-methylaminoethanol 3.4 g N-[5-((1α, 2β, 3α)-1-ethyl-6-methoxy-3-methylindan-1-yl)-2-hydroxy-3-methoxyphenylmethyl]-N-(2-hydroxyethyl)-N-methylamine; white crystals, melting point 141° C.–143° C.

$C_{24}H_{33}O_5N$ (415.33): C 69.34, H 8.03, N 3.37 (theoretical). C 69.16, H 7.96, N 3.23 (found).

EXAMPLE 6

To make the hydrochloride of the compound obtained according to Example 4, the equimolar amount of ethereal hydrochloric acid is trickled into a solution of 5 g N-[5-(trans-2,3-dihydro-7-methoxy-3-methyl-5-(E)-propenylbenzofuran-2-yl)-2-hydroxy-3-methyoxyphenylmethyl]-N-(2-hydroxyethyl)-N-methylamine in 60 ml absolute ether. The deposit is siphoned off and washed with absolute ether. 8.8 g N-[5-(trans-2,3-hydro-7-methoxy-3-methyl-5-(E)-propenylbenzofuran-2-yl)-2-hydroxy-3-methoxyphenylmethly]-N-(2-hydroxyethyl)-N-methylammoniumchloride are obtained; fine slightly yellowish hygroscopic crystals, melting point 74° C. (decomposition).

$C_{24}H_{32}ClNO_5$ (449.77): C 64.03, H 7.19, Cl 7.88, N 3.11 (theoret.). C 63.79, H 7.13, Cl 7.77, N 3.02 (found).

To prepare the aspartate one adds to a solution of 1 g N-[5-(trans-2,3-dihydro-7-methoxy-3-methyl-5-(E)-propenylbenzofuran-2-yl)-2-hydroxy-3-methoxy-phenylmethyl]-N-(2-hydroxyethyl)-N-methylamine in 25 ml ethanol 0.32 g L-aspartic acid in 15 ml hot water. It was kept for 2 hours at 70° C., the solvent subsequently being drawn off in a rotation evaporator. After drying in vacuo, a slightly brownish amorphous residue is obtained: N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylammonium aspartate.

To make the salt with lipoic acid, 0.5 g lipoic acid are added to a solution of 1 g N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylamine in 50 ml methanol and stirred for hours to achieve complete homogenization; after evaporation of the methanol and drying in vacuo, a light brown amorphous residue is obtained.

EXAMPLE 7

3.9 g ornithine are dissolved in 200 ml water and treated with a solution of 10 g trans-2,3-dihydro-2-(3,4-dimethoxyphenyl)-7-methoxy-3-methylbenzofuran-5-carbonic acid in 2 liters ethanol. The initially clear solution starts to turn turbid after about 30 minutes and a voluminous deposit begins to form, which is siphoned off after 2 hours and washed with 95 percent ethanol and dried. After recrystallization from water/acetone, 10 g colorless crystals of C-ornithine trans-2,3-dihydro-2-(3,-4-dimethoxyphenyl)-7-methoxy-3-methyl-benzofuran-5-carboxylate, melting point 192°–193° C. (decomposed) are obtained $C_{24}H_{32}N_2O_8$ (476.32): C 60.46, H 6.79, N 5.88. C 60.19, H 6.66, N 5.79.

Preparation of the starting material 40 g trans-2,3-dihydro-2-(4-hydroxy-3-methoxyphenyl)-7-methoxy-3-methyl-5-(E)-propenylbenzofuran are treated in 800 ml 95 percent ethanol with 30 ml dimethylsulphate and thereafter gradually shaken with a total of 48 ml 30 percent potassium lye without exceeding the temperature of 40° C. Thereafter, stirring for 12 hours at room temperature and dilution with 1 liter water. The resulting sediment is siphoned off and washed with water. After recrystallization from ethanol, 34.8 g trans-2,3-dihydro-2-(3,4-dimethoxyphenyl)-7-methoxy-3-methyl-5-(E)-propenylbenzofuran are obtained; melting point 124° C.

There is gradually added to 15 g of this methylated product in 300 ml absolute acetone a total of 21 g potassium permanganate within 16 hours under agitation and cooling with ice, the acetone being evaporated in vacuo in a rotation evaporator, the residue suspended in 600 ml water, and sulphur dioxide being passed until the solution turns yellow, with the manganese dioxide going into solution and a new flaky deposit being formed. The latter is separated, washed with water, digested with 600 ml 10 percent sodium lye, certrifuged from the insoluble part and the residue digested four times with 200 ml water. The combined aqueous-alkaline phases are acidified with dilute hydrochloride acid and, after recrystallization, initially from acetic ester/petroleum ether (boiling point 60°–80° C.), then from glacial acetic acid, 6.4 g trans-2,3-dihydro-2-(3,4-dimethoxyphenyl)-7-methoxy-3-methylbenzofuran-5-carbonic acid, melting point 135°–136° C., are obtained.

To set free L-ornithine, the corresponding hydrochloride is applied to an ion exchanger column with AMBERLITE 120 (trademark) in the $NH_4^+$ form, then eluted with 5 percent ammonia, all volatile materials being evaporated in vacuo.

To make the salt with L-arginine, a solution of 5.1 g L-arginine in 200 ml water are treated with 10 g trans-2,3-dihydro-2-(3,4-dimethoxyphenyl)-7-methoxy-3-methylbenzofuran5-carbonic acid in 500 ml 95 percent ethanol. The solution is heated for two hours at 60° C., then the solvent removed in vacuo with a slightly yellowish crystalline residue remaining: L-arginine trans-2,3-dihydro-2-(3,4-dimethoxyphenyl)-7-methoxy-3-methylbenzofuran-5-carboxylate-monohydrate, melting point 130°–135° C.

$C_{24}H_{34}N_4O_8 \cdot H_2O$ (536.40): C 55.93, H 6.78 (theoretical). C 55.56, H 6.82 (found).

To make the salt with choline, 4.1 g cholinechloride in 150 ml absolute ethanol are treated with 1.6 g KOH in 6 ml water with stirring, filtered after 2 hours from the precipitated KCl and rewashed with absolute ether. To this solution are trickled 10 g trans-2,3-dihydro-2-(3,4-dimethoxyphenyl)-7-methoxy-3-methylbenzofuran-5-carbonic acid in 500 ml absolute ethanol and subsequently kept at 65° C. for 1 hour. Subsequent concentration in vacuo and addition of diethylether yield 13 g choline trans-2,3-dihydro-2-(3,4-dimethoxyphenyl)-7-methoxy-3-methylbenzofuran-5-carboxylate-monohydrate.

Melting point 163°–165° C.

$C_{24}H_{33}NO_5 \cdot H_2O$ (465.38): C 61.89, H 7.59 (theoretical). C 61.84, H 7.48 (found).

EXAMPLE 8

In a nitrogen atmosphere 10 g trans-2,3-dihydro-2-(4-hydroxy-3-methoxyphenyl)-7-methoxy-3-methyl-5-(E)-propenylbenzofuran are dissolved in 400 ml 2 N potash lye and treated with 37 ml 35 percent formalin solution, then held for 24 hours at 74° C. and treated twice within this period with the same amount of formaline solution. After cooling follows acidification with dilute hydrochloric acid until a pH of 1 is attained, then extraction with ether, washing of the ether phase with water, 5 percent $NaHCO_3$ solution and water, and drying over $Na_2SO_4$. The oil remaining upon removal of the ether is crystallized from methylenechloride/petroleum ether (boiling point 60°–80° C.) and yields 7 g 5-[trans-2,3-dihydro-7-methoxy-3-methyl-5-(E)-propenylbenzofuran-2-yl]-2-hydroxy-3-methoxybenzyl alcohol, melting point 117°–119° C.

$C_{21}H_{24}O_5$ (356.24): C 70.74 H, 6.80 (theoretical). C 70.93 H, 6.67 (found).

EXAMPLE 9

In a nitrogen atmosphere 10 g 5-[trans-2,3-dihydro-7-methoxy-3-methyl-5-(E)-propenylbenzofuran-2-yl]-2-hydroxy-3-methoxybenzyl alcohol are dissolved in 400 ml 1 N potash lye and kept at 120° C. for 24 hours. After cooling follows acidification with dilute hydrochloric acid until a pH of 4 is attained, then extraction with ether, the ether phase being washed with water, 5 percent $NaHCO_3$ solution and water, and dried over $Na_2SO_4$. The light brown oil remaining after removal of the ether in vacuo is purified chromatographically over a column and yields after crystallization from methylene chloride/petroleum ether (boiling point 60°–80°) 4.5 g Bis-[5-(trans-2,3-dihydro-7-methoxy-3-methyl-5-(E)-propenylbenzofuran-2-yl)-2-hydroxy-3-methoxyphenyl]-methane, colorless crystals. Melting point 101° C. (decomposition).

$C_{41}H_{44}O_8$ (664.44): C 74.05, H 6.69 (theoretical). C 74.52, H 6.81 (found).

EXAMPLE 10

Preparation of 10,000 tablets, each having a content of 50 mg of the active substance.

Components trans-2,3-dihydro-2-(4-hydroxy-3-methoxyphenyl-7-methoxy-3-methyl-5-(E)-propenylbenzofuran: 500 g
lactose: 1700 g
corn starch: 90 g
polyethylene glycocoll 6000: 90 g
talcum powder: 90 g
magnesium stearate: 30 g

Process

The powdered constituents are sifted with a 0.6-mm mesh sieve. The active substance is then mixed in a suitable mixer with lactose, talcum, magnesium, stearate and with half the starch. The other half of the starch is suspended in 50 ml water, the suspension being poured into a 80° C. hot solution of the polyethylene glycocoll in 190 mm water. The resulting paste is added to the mixture of the powdered constituents and granulated, in some circumstances mixed with an additional amount of water. The granulate is dried for 12 hours at 30° C., driven through a 1.2-mm-mesh sieve and pressed into 7-mm tablets. Preparation of 10,000 capsules, each having a content of 100 mg of the active substance:

Constituents

N-[5-trans-2,3-dihydro-7-methoxy-3-methyl-5-(E)-propenylbenzofuran-2-yl)-2-hydroxy-3-methoxyphenylmethyl]-N-(2-hydroxyethyl)-N-methylamine: 1000 g
lactose: 2800 g
talcum powder: 200 g

Process

The powder constituents are sifted with a 0.6-mm-mesh sieve. The active substance is homogenized in a mixer, first with the talcum powder and then with the lactose. Using a filling machine, gelatin capsules of corresponding size are filled with 400 mg of the mixture.

Preparation of 10,000 ml injection solution for filling in ampoules:

Constituents

N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylammoniumchloride: 600 g
sodium chloride: 10 g
aqua pro injectione: ad 10,000 ml

Process

Upon dissolution of the constituents, filtration through a glass suction filter with a permeability of G3 and filling in ampoules in a nitrogen atmosphere: if used for intravenous injections in 2-ml ampoules, and if used as addition to infusions in 5-ml ampoules.

EXAMPLE 11

15 g of trans-2,3-dihydro-2-(4-hydroxy-3-methoxyphenyl)-7-methoxy-3-methyl-5-(E)-propenylbenzofurane("Dehydrodiisoeugenol") are dissolved in 150 ml abs. toluene at 80°. 9.5 g of N,N-dimethyl-2-chloroethylamine-hydrochloride and 15.5 g KOH in solid form are added. After 6 h at 80°, the solution is cooled down and decanted from solid KOH, whereafter the toluene solution is washed with water to remove dissolved KOH. After drying over sodium sulfate, the solution is evaporated in vacuo. The residue is cristallized in vacuo, and the still present non-cristalline part is dissolved in petroleum ether. One obtains 11.2 g of N-2-[4-(trans-2,3-dihydro-7-methoxy-3-methyl-5-(E)-propenylbenzofurane-2-yl)-2-methoxyphenoxy]ethyl-N,N,-dimethylamine, as slightly yellow cristals of mp 58°-60° C.

$C_{24}H_{31}O_4N$ (397,22): calc. C 72.49, H 7.88, N 3.52. found C 72.29, H 7.91, N 3.39.

EXAMPLE 12

10 g of the compound obtained according to example 11 are dissolved in 200 ml of abs. ether, and an equimolar amount of etheric hydrochloric acid is added dropwise. The precipitate thus obtained is partly non-cristalline, but cristallises completely within 24 h. The cristals are filtered off and washed with abs. ether. One obtains 10.0 g of N-2-[4-(trans-2,3-dihydro-7-methoxy-3-methyl-5-(E)-propenyl-benzofurane-2-yl)-2-methoxyphenoxy]ethyl-N,N-dimethylammoniumchloride as slightly yellow hygroscopic cristals, mp 135.5°-137° C.

$C_{24}H_{32}ClNO_4$ (433,78): calc. C 66.39, H 7.45, Cl 8.17. found C 66.20, H 7.36, Cl 8.31.

In the galactosamine test already mentioned N-2-[4-(trans-2,3-dihydro-7-methoxy-3-methyl-5-(E)-propenylbenzofuran-2-yl)-2-methoxyphenoxy]-ethyl-N,N-dimethylammonium chloride displayed a pharmacological activity similar to that of N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylammonium chloride but proved to possess superior stability in stress experiments.

What we claim is:

1. A dilignol and dilignol type compound having the formula

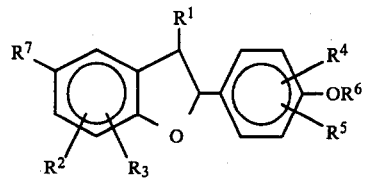

and their salts with pharmaceutically acceptable acids, wherein:
$R^1$ is lower alkyl,
$R^2$, $R^3$ and $R^4$ are independently hydrogen, hydroxy or methoxy,
$R^5$ and $R^6$ are hydrogen or a lower unbranched or branched alkyl group bearing an amino group substituted by two lower alkyl groups or by lower hydroxyalkyl or carboxyalkyl groups or combinations thereof, with the proviso that not both $R^5$ and $R^6$ are hydrogen and that if one of $R^5$ or $R^6$ is hydrogen, the other is said amino bearing lower alkyl group, and $R^7$ is —CH=CH—$R^1$.

2. N-[5-(trans,2,3-dihydro-7-methoxy-3-methyl-5-(E)-propenylbenzofuran-2-yl)-2-hydroxy-3-methoxyphenylmethyl]-N(2-hydroxyethyl)-N-methylammonium-L-aspartate, and the Salt of N-[5-(trans-2,3-dihydro-7-methoxy-3-methyl-5-(E)-propenylbenzofuran-2-yl)-2-hydroxy-3-methoxy-phenylmethyl]-N-(2-hydroxyethyl)-N-methylamine with α-liponic acid.

3. [4-(trans-2,3-dihydro-7-methoxy-3-methoxy-3-methyl-5-(E)-propenylbenzofurane-2-yl)-2-methoxyphenoxy]ethyl-N,N-dimethylamine, and its hydrochloride.

4. N-[5-(trans-2,3-dihydro-7-methoxy-3-methyl-5-(E)-propenylbenzofuran-2-yl)-2-hydroxy-3methoxyphenyl-methyl]-N-methylglycine, N-[5-(trans-2,3-dihydro-7-methoxy-3-methyl-5-(E)-propenylbenzofuran-2-yl)-2-hydroxy-3-methoxyphenylmethyl]-N-(2-hydroxyethyl)-N-methylamine, and N-[5-(trans-2,3-dihydro-7-methoxy-3-methyl-5-(E)-propenylbenzofuran-2-yl)-2-hydroxy-3-methoxyphenylmethy]-N-(2-hydroxy ethyl)-N-methylammoniumchloride.

5. A method for treating an animal or human being suffering from liver diseases, comprising administering to said animal or human being a pharmaceutically effective amount of a compound consisting of the class comprising N-[5-(trans-2,3-dihydro-7-methoxy-3-methyl-5-(E)-propenylbenzofuran-2-yl)-2-hydroxy-3-methoxyphenylmethyl]-N-methylglycine;

N-[5-(trans-2,3-dihydro-7-methoxy-3-methyl-5-(E)-propenylbenzofuran-2-yl)-2-hydroxy-3-methoxyphenylmethyl]-N-(2-hydroxyethyl N-methylamine;

N-[5-(trans-2,3-dihydro-7-methoxy-3-methyl-5-(E)-propenylbenzofuran-2-yl)-2-hydroxy-3-methoxyphenylmethyl]-N-(2-hydroxyethyl-N-methylammonium chloride;

salts N-[5-(trans-2,3-dihydro7-methoxy-3-methyl-5-(E)-propenyl-benzofuran-2-yl)-2-hydroxy-3-methoxyphenylmethyl]-N-(2-hydroxyethyl)-N-methylammonium-L-aspartate, and salt of N-[5-(trans-2,3-dihydro-7-methoxy-3-methyl)-5-(E)-propenyl-benzofuran-2-yl)-2-hydroxy-3-methoxyphenylmethyl]-N-(2-hydroxyethyl)-N-methylamine with α-liponic acid.

* * * * *